United States Patent
Goto

(10) Patent No.: US 6,262,312 B1
(45) Date of Patent: Jul. 17, 2001

(54) PROCESS FOR PRODUCING 1,1,1-TRIFLUOROACETONE

(75) Inventor: Yoshihiko Goto, Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/578,901

(22) Filed: May 26, 2000

(30) Foreign Application Priority Data

May 27, 1999 (JP) .................................................. 11-147670

(51) Int. Cl.⁷ .................................................. C07C 45/63
(52) U.S. Cl. ............................................ 568/394; 568/411
(58) Field of Search ..................................... 568/394, 411

(56) References Cited

U.S. PATENT DOCUMENTS

| | | | |
|---|---|---|---|
| 4,060,555 | * | 11/1977 | Peterson et al. . |
| 5,093,532 | * | 3/1992 | Baasner et al. . |
| 5,481,029 | * | 1/1996 | Braun et al. . |

OTHER PUBLICATIONS

Sykes et al., "a New Synthesis of Fluoro–ketones", J. Chem. Soc., pp. 835–839 (1956).

Burdon et al., "the sodium–Promoted claisen Ester Condensations of Ethyl Perfluoroalkanecarboxylates", Tetrahedron, vol. 20, pp. 2163–2166 (1964).

Yamana et al., "A Convenient Synthesis of 2,2–Difluoro Enol Silyl Ethers from Chlorodifluoromethyl Ketones", & Tetrahedron, vol. 24, No. 5 p 507–510 (1983).

* cited by examiner

Primary Examiner—Johann Richter
Assistant Examiner—Sikarl A. Witherspoon
(74) Attorney, Agent, or Firm—Crowell & Moring, L.L.P.

(57) ABSTRACT

The invention relates to a process for producing 1,1,1-trifluoroacetone. This process includes reacting a halogenated acetone with a metal in the presence of a proton donor. This halogenated acetone is represented by the general formula (1):

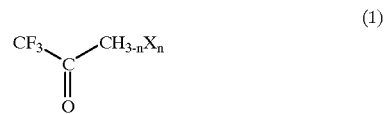

(1)

where X represents a chlorine atom, bromine atom or iodine atom, and n represents an integer from 1 to 3. It is possible to easily obtain 1,1,1-trifluoracetone from the halogenated acetone, which is easily available.

14 Claims, No Drawings

PROCESS FOR PRODUCING 1,1,1-TRIFLUOROACETONE

BACKGROUND OF THE INVENTION

The present invention relates to a process for producing 1,1,1-trifluoroacetone that is useful as an intermediate of pharmaceuticals and agricultural chemicals, or as a reagent for introducing fluorine-containing groups.

1,1,1-trifluoroacetone is known to be obtained by various methods. It is described in J. Chem. Soc. (Lond.) 1956, 835 that 1,1,1-trifluoroacetone is synthesized by a Grignard reaction between trifluoroacetic acid and magnesium methyliodide. This Grignard reaction must be conducted in an anhydrous state. In addition, it is also described in Tetrahedron, 20, 2163 (1964) that trifluoroacetone can be synthesized by decarbonating trifluoroacetoethyl acetate in sulfuric acid. It is described in Tetrahedron Lett. Vol. 24 (No. 5), 507–510, 1983 that difluoromethylketones are obtained at considerably high yield as a result of reducing chlorodifluoroketones, which are represented by $CF_2ClC(=O)R$ (wherein R is a group not containing halogen) by zinc and methanol in tetrahydrofuran.

SUMMARY OF THE INVENTION

It is an object of the present invention to provide a process for easily producing 1,1,1-trifluoroacetone from a raw material, which is easily available, such as a chlorofluorinated acetone.

According to the present invention, there is provided a process for producing 1,1,1-trifluoroacetone. This process includes reacting a halogenated acetone with a metal in the presence of a proton donor. This halogenated acetone is represented by the general formula (1):

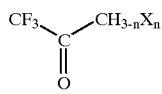

(1)

where X represents a chlorine atom, bromine atom or iodine atom, and n represents an integer from 1 to 3.

According to the present invention, it is possible to obtain 1,1,1-trifluoroacetone by the above-mentioned simple procedure from the halogenated acetone, which is easily available.

DESCRIPTION OF THE PREFERRED EMBODIMENTS

Although X (halogen atom) of the halogenated acetone represented by the general formula (1) is chlorine, bromine or iodine, and the reaction proceeds easily in that order (i.e., Cl<Br<I is easiness), it is the most preferable in practice to use a compound represented by the general formula (2):

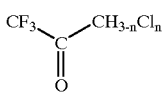

(2)

where n is an integer from 1 to 3. More specifically, this compound is either 3-chloro-1,1,1-trifluoroacetone, 3,3-dichloro-1,1,1-trifluoroacetone or 3,3,3-trichloro-1,1,1-trifluoroacetone. In the process of the present invention, the compound may be that in which the chlorine has been replaced with bromine.

The halogenated acetone used as starting material in the process of the present invention may be a hydrate, alcohol addition product, gem-diol, acetal or hemiacetal, or their aqueous or alcohol solutions, of a halogenated acetone represented by the general formula (1), as indicated in the following formulas, although an aqueous solution is preferable due to its ease of handling:

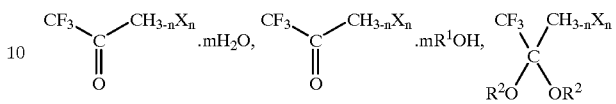

where X and n are the same as previously defined in the general formula (1), m represents an integer, $R^1$ represents an alkyl group, and each $R^2$ independently represents a hydrogen atom or alkyl group.

The halogenated acetone represented by the general formula (1) may be produced by any method. For example, 3,3-dichloro-1,1,1-trifluoroacetone is obtained by fluorinating pentachloroacetone by hydrogen fluoride in the presence of a catalyst such as antimony. Similarly, 3-chloro-1,1,1-trifluoroacetone and 3,3,3-trichloro-1,1,1-trifluoroacetone are respectively obtained from 1,1,1,3-tetrachloroacetone and hexachloroacetone. In addition, it is possible to use other halogenated acetones formed as by-products during these fluorinations.

The metal used in the process of the present invention is a low-valence metal, examples of which include zinc, aluminum, magnesium, iron, sodium and potassium. Among these, zinc is the most preferable. The metal is not particularly necessary to be of high purity, and that having ordinary purity can be used without impairment. The metal may be in any form, examples of which include a powder, particles, strips, rods, small clumps or small sheets. Normally, commercially available zinc powder, which is used industrially, is used preferably.

The metal used in the reaction is in an amount of preferably at least 0.5 n moles, more preferably at least n moles, for example, from n to about 10 n moles, per mole of the halogenated acetone, where n is the number as defined in the general formula (1). If the amount of the metal is less than 0.5 n, the reaction is not completed. On the other hand, although the use of an excess amount of the metal does not cause a problem in terms of the reaction, it is unnecessary.

The proton donor used in the present invention is water or an alcohol or ether that is miscible with water. Its examples include alcohols such as methyl alcohol, ethyl alcohol, i-propyl alcohol and n-propyl alcohol, and ethers such as di-n-butylether and dioxane. These can also be used in combination. Since the proton donor also has the role of a solvent for allowing the reaction to proceed easily in addition to its inherent role as a reaction reagent, use of an excess amount of the proton donor does not generally cause a problem. Its amount is normally determined from the viewpoint of using it as solvent. Thus, the proton donor used in the reaction is in an amount of preferably at least 0.5 n moles, more preferably at least n moles, relative to 1 mole of the halogenated acetone represented by the general formula (1), where n is the number as defined therein. These proton donor and metal can be used with an inorganic acid such as hydrochloric acid or sulfuric acid, or a metal chloride or metal sulfate such as zinc chloride.

The process of the present invention can be carried out at a temperature of from 0° C. to the reflux temperature. In the case of carrying out at normal pressure, it can be carried out at 0–100° C., preferably from room temperature without performing any heating or cooling to about 100° C., more preferably within the range of about 50–100° C. If the reaction temperature is lower than 0° C., the reaction rate may become too slow causing an excess amount of time to be required for the reaction, thereby making this undesirable. In addition, it is preferable from the viewpoint of product recovery to carry out the reaction at a temperature equal to or higher than the boiling point of the product. The reaction pressure may be 1–20 kg/cm$^2$ (0.1–2.0 MPa). If the reaction pressure is increased, the reaction temperature can be raised. With this, the reaction time can be shortened.

The process of the present invention can be carried out by charging the respective predetermined amounts of a halogenated acetone represented by the general formula (1), metal and proton donor into a reaction vessel that can be sealed and then by heating to the predetermined temperature. Alternatively, the process of the present invention can be carried out by charging the respective predetermined amounts of metal and proton donor into a reaction vessel that can be sealed, then heating to the predetermined temperature, and then continuously or intermittently adding a halogenated acetone represented by the general formula (1) thereto. Recovery of the product can be performed either by allowing 1,1,1-trifluoroacetone to flow out of the reaction solution after stopping the reaction, or by allowing 1,1,1-trifluoroacetone, which is a low-boiling-point compound, to flow out of the reaction vessel as it is formed during the reaction. The thus recovered crude 1,1,1-trifluoroacetone may contain the proton donor and by-products. However, these can be removed by distillation to obtain 1,1,1-trifluoroacetone of high purity.

The purification of the crude 1,1,1-trifluoroacetone is preferably conducted, as follows. At first, the crude 1,1,1-trifluoroacetone is dissolved in water to obtain an aqueous solution, followed by the addition of a metal salt, preferably an alkali metal halide or alkali-earth metal halide. The resulting mixture is heated to obtain 1,1,1-trifluoroacetone in the form of gas, followed by condensation in a container. Examples of the alkali metal halide are lithium chloride and lithium bromide. Examples of the alkali-earth metal halide are magnesium chloride, calcium chloride, strontium chloride, magnesium bromide, calcium bromide, and magnesium sulfate. Of these, calcium chloride, magnesium chloride and magnesium sulfate are particularly preferable from the viewpoints of the dehydration efficiency and the production cost. The amount of the metal salt may be in a range of 0.001–10 moles, preferably 0.01–1 mole, relative to 1 mole of water contained in the aqueous solution of the crude 1,1,1-trifluoroacetone. The above-mentioned purification may be combined with another conventional purification such as distillation or rectification, in order to obtain 1,1,1-trifluoroacetone of high purity.

The following nonlimitative examples are illustrative of the present invention.

EXAMPLE 1

30 g (0.46 moles) of zinc powder were placed in a glass reactor equipped with a dropping funnel, thermometer and packed column. 60 g of water were then added followed by stirring to suspend the zinc powder. This zinc suspension was heated to 85° C. after which 100 g of a 48% aqueous solution of 3-chloro-1,1,1-trifluoroacetone (0.33 moles) were dropped in over the course of 1.5 hours from the dropping funnel. The resulting 1,1,1-trifluoroacetone was allowed to flow out of the top of the packed column and condensed in a trap cooled to −78° C. The weight of the condensed liquid was 31.0 g, and it was found by gas chromatography to contain 82.1% 1,1,1-trifluoroacetone, 15.5% 1,1-difluoracetone and 0.9% monofluoroacetone. The yield of 1,1,1-trifluoracetone was 72%. This liquid was then purified by distillation to obtain 17.8 g of 1,1,1-trifluoroacetone having a purity of 97%.

EXAMPLE 2

50 g of zinc powder were placed in a glass reactor equipped with a dropping funnel, thermometer and packed column, 70 g of water were then added followed by stirring to suspend the zinc powder. This zinc suspension was heated to 85° C. after which 70.5 g of a 75% aqueous solution of 3,3-dichloro-1,1,1-trifluoroacetone were dropped in over the course of 1.5 hours from the dropping funnel. The resulting 1,1,1-trifluoroacetone was allowed to flow out of the top of the packed column and condensed in a trap cooled to −78° C. The weight of the condensed liquid was 28.1 g, and it was found by gas chromatography analysis to contain 80.9% 1,1,1-trifluoroacetone, 14.7% 1,1-difluoroacetone and 1.7% monofluoroacetone. The yield of 1,1,1-trifluoroacetone was 68%. This liquid was then purified by distillation to obtain 15.9 g of 1,1,1-trifluoroacetone having a purity of 97%.

EXAMPLE 3

76.5 g of zinc powder were placed in a glass reactor equipped with a dropping funnel, thermometer and packed column. 110 g of water were then added followed by stirring to suspend the zinc powder. This zinc suspension was heated to 85° C. after which 80.8 g of a 80% aqueous solution of 3,3,3,-trichloro-1,1,1-trifluoroacetone were dropped in over the course of 2 hours from the dropping funnel. The resulting 1,1,1-trifluoroacetone was allowed to flow out of the top of the packed column and condensed in a trap cooled to −78° C. The weight of the condensed liquid was 31.5 g, and it was found by gas chromatography to contain 64.7% 1,1,1-trifluoroacetone, 15.4% 1,1-difluoroacetone and 4.9% monofluoroacetone. The yield of 1,1,1-trifluoroacetone was 61%. This liquid was then purified by distillation to obtain 14.3 g of 1,1,1-trifluoroacetone having a purity of 95%.

EXAMPLE 4

55 g of zinc powder were placed in a glass reactor equipped with a dropping funnel, thermometer and packed column. 200 g of water were then added followed by stirring to suspend the zinc powder. This zinc suspension was heated to 85° C. after which 80 g of a 75% aqueous solution of a chlorinated 1,1,1-trifluoroacetone mixture, that is a mixture of 10.5% 3-chloro-1,1,1-trifluoroacetone, 78.3% 3,3-dichloro-1,1,1-trifluoroacetone and 10.1% 3,3,3-trichloro-1,1,1-trifluoroacetone, were dropped in over the course of 1.5 hours from the dropping funnel. The resulting 1,1,1-trifluoroacetone was allowed to flow out of the top of the packed column and condensed in a trap cooled to −78° C. The weight of the condensed liquid was 29.5 g, and it was found by gas chromatography to contain 77.0% 1,1,1-trifluoroacetone, 16.6% 1,1-difluoroacetone and 1.2% monofluoroacetone. The yield of 1,1,1-trifluoroacetone was 61%. This liquid was then purified by distillation to obtain 16.2 g of 1,1,1-trifluoroacetone having a purity of 94%.

EXAMPLE 5

100.0 g of zinc powder were placed in a glass reactor equipped with a dropping funnel, thermometer and packed column. 100 g of water were then added followed by stirring to suspend the zinc powder. This zinc suspension was heated to 85° C. after which 125 g of a 85% aqueous solution of a chlorinated 1,1,1-trifluoroacetone mixture, that is, a mixture of 8% 3-chloro-1,1,1-trifluoroacetone, 89% 3,3-dichloro-1,1,1-trifluoroacetone and 3% 3,3,3-trichloro-1,1,1-trifluoroacetone, were dropped from the dropping funnel. The resulting gas was collected in a pair of in-line traps each charged with 50 g water cooled to 0° C. After the collection, the contents of the traps were combined to an aqueous solution. The organic compounds recovered were determined to be 51 g, referring to a water content of the aqueous solution, measured by Karl Fischer Analysis. In other words, the water content was measured by Karl Fischer Analysis, and the total weight of the organic compounds was determined by subtracting the water content from the aqueous solution. The aqueous solution was found by gas chromatography to contain 92.9% 1,1,1-trifluoroacetone, 5,1% 1,1-difluoroacetone, and 1.1% monofluoroacetone, excluding a content of water. The yield of 1,1,1-trifluoroacetone was 86%. The aqueous solution was added to a container charged with 102 g of calcium chloride, followed by heating at 50° C. The effluent from a container was collected, and 45 g of an organic matter was obtained, containing 0.2 wt% of water. Its organic composition was found to be 94.3% 1,1,1-trifluoroacetone, 4.1% 1,1-difluoroacetone, and 0.8% monofluoroacetone. This organic matter was further rectified, thereby obtaining 36 g of 1,1,1-trifluoroacetone (purity: 99%).

What is claimed is:

1. A process for producing 1,1,1-trifluoroacetone, comprising reacting a halogenated acetone with a metal in the presence of a proton donor, said halogenated acetone being represented by the general formula (1):

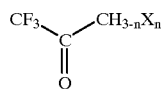

(1)

where X represents a chlorine atom, bromine atom or iodine atom, and n represents an integer from 1 to 3.

2. A process for producing 1,1,1-trifluoroacetone, comprising reacting a halogenated acetone with water and zinc, said halogenated acetone being represented by the general formula (2):

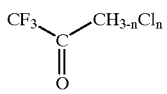

(2)

where n represents an integer from 1 to 3.

3. A process for producing 1,1,1-trifluoroacetone, comprising:
adjusting a zinc suspension comprising water and a zinc powder to having a temperature of from 50° C. to a boiling point of said zinc suspension, in a reactor;
adding a halogenated acetone continuously or intermittently to said zinc suspension having said temperature, said halogenated acetone being represented by the general formula (2), thereby obtaining a product comprising said 1,1,1-trifluoroacetone; and
removing said product continuously from said reactor,

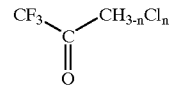

(2)

where n represents an integer from 1 to 3.

4. A process according to claim 3, wherein said adding is conducting by adding an aqueous solution containing said halogenated acetone.

5. A process according to claim 1, wherein said metal is selected from the group consisting of zinc, aluminum, magnesium, iron, sodium and potassium.

6. A process according to claim 1, wherein said metal is in an amount of at least 0.5 n moles per mole of said halogenated acetone.

7. A process according to claim 1, wherein said proton donor is at least one member selected from water, alcohols and ethers, each of said alcohols and said ethers being miscible with water.

8. A process according to claim 1, wherein said proton donor is in an amount of at least 0.5 n moles per mole of said halogenated acetone.

9. A process according to claim 1, wherein said reacting is conducted at a temperature of from 0° C. to a reflux temperature.

10. A process according to claim 1, wherein said reacting is conducted under a pressure of from 1 to 20 kg/cm$^2$.

11. A process according to claim 1, wherein a reaction product obtained by said reacting is dissolved in water, thereby obtaining an aqueous solution; and wherein a metal salt is added to said aqueous solution, followed by heating of the resulting mixture, thereby obtaining said 1,1,1-trifluoroacetone.

12. A process according to claim 11, wherein said metal salt is selected from the group consisting of alkali metal halides and alkali-earth metal halides.

13. A process according to claim 12, wherein said alkali-earth metal halides are calcium chloride, magnesium chloride and magnesium sulfate.

14. A process according to claim 11, wherein said metal salt is in an amount of 0.001–10 moles per mole of water contained in said aqueous solution.

* * * * *